United States Patent [19]

Tweedle et al.

[11] Patent Number: 5,846,519
[45] Date of Patent: Dec. 8, 1998

[54] METHOD FOR IMAGING MAMMALIAN TISSUE USING 1-SUBSTITUTED-1,4,7-TRICARBOXYMETHYL-1,4,7,10-TETRAAZACYCLODODECANE AND ANALOGS

[75] Inventors: Michael F. Tweedle, Princeton, N.J.; Glen T. Gaughan, Oxford, England; James J. Hagan, Holmdel, N.J.

[73] Assignee: Bracco Diagnostics Inc., Princeton, N.J.

[21] Appl. No.: 471,591

[22] Filed: Jun. 6, 1995

Related U.S. Application Data

[62] Division of Ser. No. 359,960, Dec. 20, 1994, Pat. No. 5,474,756, which is a continuation of Ser. No. 422,176, Oct. 16, 1989, abandoned, which is a division of Ser. No. 137,267, Dec. 23, 1987, Pat. No. 4,885,363, which is a continuation-in-part of Ser. No. 42,416, Apr. 24, 1987, abandoned, which is a continuation-in-part of Ser. No. 821,725, Jan. 23, 1986, abandoned.

[51] Int. Cl.$^6$ ...................................................... A61B 5/055
[52] U.S. Cl. ...................... 424/9.363; 514/184; 514/836; 436/173; 540/465; 540/467; 534/16
[58] Field of Search ........................ 424/9.363; 514/184, 514/836; 436/173, 806; 540/465, 467; 534/16; 128/653.4, 654

[56] References Cited

U.S. PATENT DOCUMENTS

| | | | |
|---|---|---|---|
| 3,201,472 | 8/1965 | Spivack et al. | 260/583 |
| 4,085,106 | 4/1978 | Atkins et al. | 260/256.4 |
| 4,156,683 | 5/1979 | Lehn et al. | 260/338 |
| 4,168,265 | 9/1979 | Tabushi et al. | 260/239 BC |
| 4,174,319 | 11/1979 | Kobuke et al. | 260/239 BC |
| 4,190,462 | 2/1980 | De Jong et al. | 134/2 |
| 4,543,213 | 9/1985 | Weitl et al. | 260/239 BC |
| 4,639,365 | 1/1987 | Sherry et al. | 424/9 |
| 4,647,447 | 3/1987 | Gries et al. | 424/9 |
| 4,678,667 | 7/1987 | Meares et al. | 424/85 |
| 4,719,098 | 1/1988 | Weinmann et al. | 424/9 |
| 4,826,673 | 5/1989 | Dean et al. | 424/9 |
| 4,885,363 | 12/1989 | Tweedle et al. | 540/465 |
| 4,957,939 | 9/1990 | Gries et al. | 514/492 |
| 4,963,344 | 10/1990 | Gries et al. | 424/9 |

FOREIGN PATENT DOCUMENTS

| | | |
|---|---|---|
| A 86 330/82 | 7/1982 | Australia . |
| 080 478 B1 | 5/1982 | European Pat. Off. . |
| 202 869 A | 3/1984 | Japan . |
| 210 8106 | 5/1983 | United Kingdom . |
| 213 7612 A | 1/1984 | United Kingdom . |
| WO 86/02352 | 10/1985 | WIPO . |
| WO 86/06605 | 5/1986 | WIPO . |
| WO 87/05030 | 2/1987 | WIPO . |

OTHER PUBLICATIONS

XVI International Congress of Radiology, Hawaii, USA—Jul. 8–12, 1985; New Nonionic Structures for X–Ray and MRI Contrast Agents; H. Gries, et. al.

Inorg. Chem. vol. 19, (1980) p. 1319, "Nuclear Magnetic Resonance Spectroscopy of Lanthanide Complexes with a Tetraacetic Tetraaza Macrocycle Unusual Conformation Properties", J.F. Desreux.

Inorg. Chem. vol. 23, (1984) p. 4459, "Luminescence and NMR Studies Conformational Isomers of Lanthanide Complexes with an Optically Active Polyaza Polycarboxylic Macrocycle", H. Brittain, J. Desreux.

Tetrahedron, vol. 37, (1981) p. 767, "Darstellung Und Komplexbildung Von Polyzazacycloalkan–N–Essigsauren", H. Stetter, W. Frank, R. Mertens.

Society of Magnetic Resonance in Medicine; Fifth Annual Meeting Aug. 19–22, 1986, Montreal, Quebec Canada. "Progress Toward Development of Neutral NMR Contrast". Bonnemain et. al., Chem. Abst. 108–137926Z (1988).

R.M. Kniseley et al., "Delineation of Active Marrow by Whole–Body Scanning with Radioactive Colloids", J. of Nucl. Med., 7:575–582, 1966.

C.A. Chang et. al., *JMRI* vol. 2, No. 1, pp. 95–98 (1992).

M.F. Tweedle et. al., *Radiol.*, vol. 178, No. 3, 891 (1991).

G. Gaughan, "Nonionic Gadolinium Chelates", *Enhanced Magnetic* Resonance Imaging edited by Val M. Runge, pp. 105–116 (1989).

C. Geraldes et. al., Nuclear Magnetic Resonance and Potentiometric Studies of the Protonation Scheme of a Triaza Triacetic Macrocycle and Its Complexes with Lanthanum and Lutetium, *Inorg. Chem.*, vol. 24, No. 23, pp. 3876–3881 (1985).

R.H. Knop et. al., "Gadolinium Cryptates as a new class of water soluble MRI contrast agents: Comparison to GD–DTPA for organ and pathology localization", *Soc. Magn. Reson.*, Abstracts, 871–872, Aug. 19, 1985.

*Primary Examiner*—Gary E. Hollinden
*Attorney, Agent, or Firm*—Donald L. Rhoads; George P. Hoare; Rogers & Wells

[57] ABSTRACT

A method for imaging mammalian tissue utilizing a nonionic complex of a paramagnetic ion of lanthanide element and a macrocyclic chelating agent.

19 Claims, No Drawings

METHOD FOR IMAGING MAMMALIAN TISSUE USING 1-SUBSTITUTED-1,4,7-TRICARBOXYMETHYL-1,4,7,10-TETRAAZACYCLODODECANE AND ANALOGS

This is a divisional of application Ser. No. 08/359,960, filed Dec. 20, 1994, now U.S. Pat. No. 5,474,756, which is a continuation of Ser. No. 07/422,176, filed Oct. 16, 1989, now abandoned, which is a division of Ser. No. 07/137,267, filed Dec. 23, 1987, now U.S. Pat. No. 4,885,363, which is a continuation-in-part of Ser. No. 07/042,416, filed Apr. 24, 1987, now abandoned, which is a continuation-in-part of Ser. No. 06/821,725, filed Jan. 23, 1986, now abandoned.

Metal-chelating ligands are useful in diagnostic medicine as contrast agents. X-ray imaging, radionuclide imaging, ultrasound imaging and magnetic resonance imaging can each be enhanced by the use of a metal atom bound to a chelating ligand. For example, a chelating ligand can become a radiopharmaceutical when it is prepared as a chelate complex with $^{99m}$Tc, $^{111}$In, $^{67}$Ga, $^{140}$La, $^{169}$Yb, $^{68}$Ga, $^{90}$Y, $^{188}$Re, $^{153}$Sm or other radioactive metal ions. When a chelating ligand is complexed with the stable isotopes of the lanthanides, tantalum, bismuth or other elements with molecular weight higher than iodine, the resulting complex absorbs x-rays sufficiently to act as an x-ray contrast agent. In some cases, the agents that are useful in x-ray imaging absorb, reflect or scatter ultrasound radiation sufficiently to be used as an ultrasound agent. If a chelating ligand is complexed with a paramagnetic metal atom that has a symmetric electronic ground state (e.g., $Gd^{+3}$, and octahedral $Mn^{+2}$, $Fe^{+3}$, $Cr^{+3}$) the resulting complex will be useful as a spin relaxation catalyst that is used in magnetic resonance imaging (also known as NMR imaging) as a contrast agent. If a chelating agent is complexed with a paramagnetic metal atom that has an unsymmetrical electronic ground state (e.g., dysprosium(III), holmium(III) and erbium(III)), the resulting complex will be useful as a chemical shift agent in magnetic resonance imaging or in magnetic resonance in vivo spectroscopy.

The chelating ligands can also be bi-functional. That is, they can bind tightly to the metal ion forming a chelate while at the same time bearing a second functionality which confers upon it desirable chemical, physical and/or biological properties. Desirable physical properties of the chelator differ depending on the diagnostic or therapeutic purpose of the metal chelate. Desirable physical properties common to all uses are high affinity for the metal ion bound to the chelator and ease of synthesis. When it is desired to use the metal chelate as a contrast media for NMR imaging or general purpose X-ray imaging, the desirable physical properties are high water solubility, and viscosity and osmolality of a formulated drug as close as possible to those of human blood.

Human blood has an osmolality of 0.3 Osmol/kg-water. Hyperosmolality is a well known contributor to adverse patient reactions to injected contrast media, and the lower osmolality of newer x-ray agents is due to their being nonionic molecules (possessing a net zero overall charge) (Shehadi, W H; "Contrast media adverse reactions: occurrence, reoccurrence and distribution patterns" Radiol. 1982, 143, 11–17. Bettman, M A; "Angiographic contrast agents; conventional and new media compared", Am. J. Roentgen. 1982, 139, 787–794. Bettman, M A and Morris T W; Recent advances in contrast agents, Radiol. Clin. North Am. 1986, 24, 347–357.). Gadolinium-based NMR agents in the prior art that are useful have a net negative overall charge, and therefore their aqueous formulated solutions have high osmolality. For example, $Gd(DTPA)^{2-}$ where DTPA stands for diethylenetriaminepentaacetic acid is formulated for use at 0.5M in water as the N-methylglucamine salt. The osmolality of the solution is 1.6 to 2.0 Osmol/kg-water. The preferred new gadolinium complexes of the present invention are nonionic—they are not salts. When these nonionic gadolinium complexes are formulated at 0.5M in water the osmolality of the solutions is 0.3–0.6 Osmol/Kg-water. The complex should be generally inert to interaction with the body other than general tissue distribution and excretion, usually by the renal route. These properties are also important to NMR imaging, but, in addition, the effectiveness of an agent for NMR imaging can be increased by altering the chemical structure so as to increase the ability of the metal chelate to affect the relaxation times of water protons.

In radiopharmaceutical imaging the doses administered are relatively small so that matching the drug formulation's physical properties to those of human blood is relatively unimportant. In this use biological specificity is more important. In particular, one could use $^{99m}$Tc as the metal and a chelating ligand which is functionalized with a biologically active entity such as a bile acid, fatty acid, amino acid, peptide, protein, or one of numerous chemical entities known to bind receptors in vivo. NMR contrast media may also make use of biological specificity.

In radiopharmaceutical therapy, the metal ions may be chosen from among those known in the art; for example, $^{90}$Y, $^{188}$Re, $^{153}$Sm. For this purpose the chelating ligand is generally covalently bound to a disease specific entity such as a monoclonal antibody. When the metal-chelator-antibody conjugate is injected into humans, it concentrates at the disease site, usually a malignant tumor. In this use the chelating ligand must contain a reactive functionality which allows for a covalent bond to be formed between the chelating ligand and the antibody. Important characteristics of the reactive functionality are as follows: 1) It must be covalently attached to the chelator such that it does not significantly diminish the affinity of the chelator for the metal ion. 2) It must allow simple synthesis in high yield of metal-chelator-antibody conjugates. The conjugate so-formed should have maximal affinity for its antigen, such affinity being minimally diminished as a result of covalently attaching the metal-chelator. 3) It should ideally allow for rapid excretion and/or optimal dosimetry of the radioactive metal chelator in the event that the metal-chelator-antibody conjugate is decomposed or metabolized in vivo.

When the metal is non-radioactive and paramagnetic such as gadolinium (III) the bifunctional chelate is useful in magnetic resonance imaging as a contrast agent, either as a discrete molecule or bound to substances such as lipids, sugars, alcohols, bile acids, fatty acids, receptor-binding ligands, amino acids, peptides, polypeptides, proteins, and monoclonal antibodies. When the metal is radioactive, such a yttrium(III) as $^{90}$Y, the bifunctional chelate is useful in labeling monoclonal antibodies for use in radio-therapy. When the metal is $^{99m}$Tc, $^{111}$In, $^{201}$Tl, $^{67}$Ga, $^{68}$Ga or the like, the chelate is useful in radiopharmaceutical imaging.

Two general methods have been employed for making bifunctional chelates from chelating agents. In the first method one or more carboxylic acid groups of a polyamino, polycarboxylic acid chelator are activated by conversion to such activating groups as internal or mixed anhydrides, activated esters (e.g. p nitro phenyl, N-hydroxysuccinimide, etc.) or with other derivatives known to those skilled in the art. The activated acid group is then reacted with the protein. The metal ion is then added to the protein-chelator complex.

There are two problems with this method. First, using a potential donor group, the carboxylic acid, to react with the protein can diminish the strength of the chelate and contribute to the chemical lability of the metal ion. The second problem arises because the chelating ligands have several carboxylates that are not uniquely reactive. When the chelating ligand is combined with an activating agent more than one species can result because the number and chemical position of the groups activated cannot be adequately controlled. When a mixture of such variously activated chelating ligands is added to protein, protein-chelator complexes of variable and uncertain chelating strength can be formed. Also, multiple activation of carboxylic acids on a chelator leads to intra- and inter-molecular crosslinking which is a major source of decreased immunospecificity. This problem could be overcome by separating all of the products formed from the reaction of the activating agent with the chelating ligand, but that process is very laborious and makes the overall synthesis highly inefficient.

The second method for making a bifunctional chelate is to prepare a chelating ligand with a unique reactive function, such as an isothiocyanate, attached to the chelating ligand at a position that does not substantially diminish the strength with which the chelating ligand binds the metal ion. An article entitled "Synthesis of 1-(p-isothiocyanatobenzyl) derivatives of DTPA and EDTA. Antibody Labeling and Tumor-Imaging Studies" by Martin W. Brechbiel, Otto A. Gansow, Robert W. Atcher, Jeffrey Schlom, Jose Esteban, Diane E. Simpson, David Colcher, Inorganic Chemistry, 1986, 25, 2772 is illustrative of the above second method.

BRIEF DESCRIPTION OF THE INVENTION

It is an object of this invention to provide new metal-chelating ligands.

It is an object of this invention to provide new metal chelate complexes that are nonionic.

Another object is to provide metal chelating ligands which when complexed with a metal heavier than iodine (e.g. Ba, Ta, Pb, Bi, Lanthanides) are effective as X-ray contrast agents.

Another object is to provide metal chelating ligands which when complexed with gamma emitting radioactive nuclide (e.g. $^{99m}$Tc or $^{111}$In) are effective as imaging radiopharmaceuticals.

Another object is to provide metal chelating ligands which when complexed with beta or alpha emitting radioactive nuclide (e.g. $^{90}$Y, $^{153}$Sm, $^{188}$Re, $^{212}$Bi) are effective as therapeutic radiopharmaceuticals.

It is a further object of this invention to provide metal-chelating ligands whose metal chelate complexes in acqueous solution have low osmolality.

It is a further object of this invention to provide metal-chelating ligands whose metal chelate complexes have low acute toxicity.

It is a further object of this invention to provide metal-chelating ligands which, when complexed with a paramagnetic metal atom, are effective as relaxation catalysts in magnetic resonance imaging.

It is a further object of this invention to provide bifunctional metal-chelating ligands that have the ability to covalently bind to proteins or other biologically active molecules thereby imparting biological specificity to the metal chelate complex.

It is a further object of this invention to provide bifunctional metal-chelating ligands that are themodynamically stable, kinetically inert and, when desired, electrically neutral.

These, and other objects which will be appreciated by the practitioner of this invention, are achieved by compounds having the formula

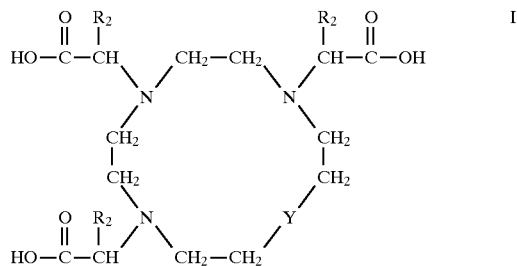

In formula I, and throughout the specification, the symbols are as defined below.

Y is oxygen or

$R_1$ is hydrogen, alkyl, arylalkyl, aryl, alkoxy, hydroxyalkyl,

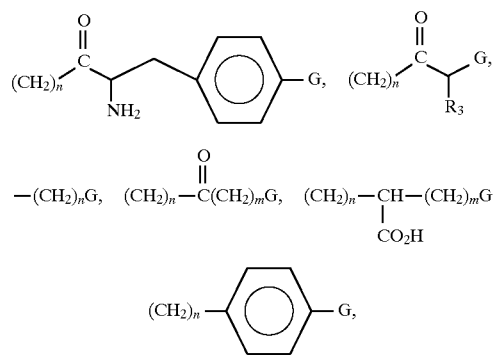

wherein G is $NH_2$, NCS,

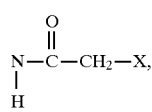

$CO_2H$
$NHR_4$, $N(R_4)_2$,CN, wherein $R_4$ is alkyl or hydroxyalkyl,

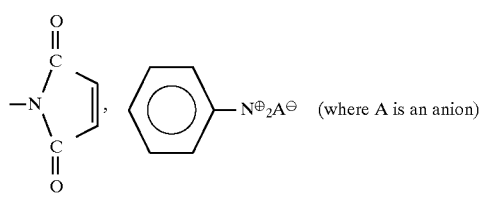

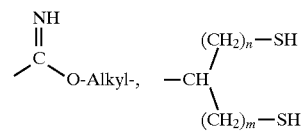

wherein n and m are zero or an integer from one to five, $R_2$ is hydrogen or alkyl, $R_3$ is hydrogen, hydroxyalkyl, alkoxy, alkyl, aryl or arylkyl and X is chloro, bromo or iodo.

Preferred embodiments for when the compounds are linked to a protein are when n=2 or 1 and G=NCS.

It is understood that other functional groups known in the art can be used to link the bifunctional metal-chelating ligands of this invention to monoclonal antibodies or fragments thereof.

$R_1$ and $R_2$ are hydrogen in a preferred embodiment for forming a Gd(III) chelate useful in general purpose magnetic resonance imaging. The most prefered embodiment for forming a Gd(III) chelate is when $R_1$ is hydroxyalkyl or when $R_1$ is

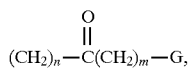

wherein n is 1, m is 0, G is $NHR_4$ wherein $R_4$ is alkyl.

The terms "alkyl" and "alkoxy" as used throughout the specification, refer to both straight and branched chain groups. Those groups having 1 to 5 carbon atoms are preferred and methyl is the most preferred alkyl group.

The term "aryl" as used throughout the specification refers to phenyl and substituted phenyl. Preferred substituted phenyl groups are those substituted with 1, 2 or 3 halogen, hydroxyl, alkyl, alkoxy, carbamoyl or carboxyl groups.

Hydroxyalkyl refers to straight and branched alkyl bearing radicals R—OH groups such as —$CH_2CH_2OH$, —$CH_2CH_2$ $OHCH_2OH$, $CH(CH_2OH)_2$ and the like. Such chemistry is well known to those skilled in the art (Sovak, M. editor Radiocontrast Agents, Springer-Venlag, 1984 pp. 1–125.

DETAILED DESCRIPTION OF THE INVENTION

The compounds of formula I, and salts thereof, can be complexed with a paramagnetic metal atom and used as relaxation enhancement agents for magnetic resonance imaging. These agents, when administered to a mammalian host (e.g., humans) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times generally before and after administration of the agents, and the differences in the images created by the agents' presence in tissues are used in diagnosis. In proton magnetic resonance imaging, paramagnetic metal atoms such as gadolinium(III), and octahedral manganese (II), chromium (III), and iron(III) (all are paramagnetic metal atoms with a symmetrical electronic configuration) are preferred as metals complexed by the ligands of formula I; gadolinium (III) is most preferred due to the fact that it has the highest paramagnetism, low toxicity, and high lability of coordinated water.

The metal-chelating ligands of formula I can be complexed with a lanthanide (atomic number 58 to 71) and used as chemical shift agents in magnetic resonance imaging or in magnetic resonance in vivo spectroscopy.

While the above-described uses for the metal-chelating ligands of formula I are preferred, those working in the diagnostic arts will appreciate that the ligands can also be complexed with the appropriate metals and used as contrast agents in x-ray imaging, radionuclide imaging and ultrasound imaging.

USE IN IMAGING

To use the ligands of this invention for imaging, they must first be complexed with the appropriate metal. This can be accomplished by methodology known in the art. For example, the metal can be added to water in the form of an oxide or in the form of a halide and treated with an equimolar amount of a ligand of formula I. The ligand can be added as an aqueous solution or suspension. Dilute acid or base can be added (if needed) to maintain a neutral pH. Heating at temperatures as high as 100° C. for periods up to four hours is sometimes required, depending on the metal and the chelator, and their concentrations.

Pharmaceutically acceptable salts of the metal complexes of the ligands of this invention are also useful as imaging agents. They can be prepared by using a base (e.g., an alkali metal hydroxide, meglumine or arginine) to neutralize the above-prepared metal complexes while they are still in solution. Some of the metal complexes are formally uncharged and do not need cations as counterions. Such neutral complexes are preferred as intravenously administered x-ray and NMR imaging agents over charged complexes because they provide solutions of greater physiologic tolerance due to their lower osmolality.

Sterile aqueous solutions of the chelate-complexes can be administered to mammals (e.g., humans) orally, intrathecally and especially intravenously in concentrations of 0.003 to 1.0 molar. For example, for the visualization of brain lesions in canines using magnetic resonance imaging, a gadolinium complex of a ligand of formula I can be administered intravenously at a dose of 0.05 to 0.5 millimoles of the complex per kilogram of animal body weight, preferably at a dose of 0.1 to 0.25 millimole/kilogram. For visualization of the kidneys, the dose is preferably 0.05 to 0.25 millimoles/kilogram. For visualization of the heart, the dose is preferably 0.25 to 1.0 millimoles/kilogram. The pH of the formulation will be between about 6.0 and 8.0, preferably between about 6.5 and 7.5. Physiologically acceptable buffers (e.g., tris(hydroxymethyl)aminomethane) and other physiologically acceptable additives (e.g., stabilizers such as parabens) can be present.

Use in Radiotherapy or Imaging Where the Metal-Chelate-Complex is Bound to a Biomolecule The bifunctional metal-chelating ligands can bind to a monoclonal antibody or a fragment thereof for use in radiotherapy. Monoclonal antibodies are useful in that they can be used to target radio-nuclides to cancer or tumor sites with great specificity. The compounds of this invention wherein $R_1$ is other than hydrogen are then linked to monoclonal antibodies or fragments thereof.

The methods of linking the bifunctional chelate to the antibody or antibody fragment are known in the art (Brechbiel, same reference as referred to hereinabove) and will depend primarily on the particular bifunctional chelate and secondarily on the antibody or fragment thereof. For example, when the formula I compound is

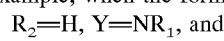, $Y=NR_1$, and

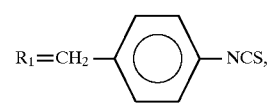

one reacts 10 μl of a 5.0 mM aqueous solution of the formula I chelator with 0.5 ml of a 5.0 mg/ml monoclonal antibody (B72.3 purchaseable from Damon Biotech Corporation) in 50 mM Hepes buffer at pH 8.5. 16 μl of 1.5M aqueous triethylamine is added. After 2 hours reaction time, the monoclonal antibody is purified by dialysis. This procedure provides between 1 and 2 formula I chelator molecules bound to each monoclonal antibody. Radioactive metal ion (for example $^{90}Y$) can then be added to the monoclonal antibody-bound chelator by methods known in the art. For example, $^{90}Y$ as the $^{90}Y(III)(acetate)_3(H_2O)_4$ (approximate formula in aqueous solution) can be reacted with the monoclonal antibody-bound chelate in solutions where the concentration of each is between $10^{-5}$–$10^{-7}$ and the pH is 6. Dialysis against citrate is then used to purify the product.

An alternative, and preferred method follows that described above, but substitutes the metal-chelate complex for the chelating ligand. To use this method the metal chelate complex is first made by reacting Metal-oxide, -halide, nitrate -acetate, or the like with Formula I chelator. For the chelator described above the acetate of $^{90}Y$ at $<10^{-6}M$ is reacted with the chelator at about $10^{-3}$ at pH 6, the chelate complex is purified by ion exchange or reverse phase HPLC chromatography, and then reacted with the monoclonal antibody described above for the chelator. The bifunctional, metal-containing, linked antibody is used in the following manner. A human or animal with a tumor to which the monoclonal antibody is specific is injected intravenously, subcutaneously, intraparetoneally or intralymphatically for example, with an aqueous solution of the $^{90}Y$-formula I chelator-monoclonal antibody compound. This allows the radioactive metal ion to be directed to the tumor for which it is intended. The intravenous dosaged used is 0.1 to 0.4 millicurie per kilogram of body weight.

Preparation of Formula I Compounds

The compounds of formula I can be prepared by the reaction of a compound having the formula

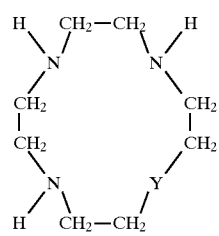
II with a reactive acid derivative having the formula

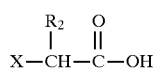
III wherein X is a readily displaceable group such as chlorine, bromine or iodine.

In preparing those compounds of formula I wherein Y is oxygen or

other than —NH—, the above-described reaction of a compound of formula II with a compound of formula III is preferably carried out in water at a pH of about 9 to 10 (most preferably about 9.5). The reaction proceeds most readily if it is warmed to about 50°–80° C. Base, such as an alkali metal hydroxide or a tetra-alkylammonium hydroxide, can be used to adjust and maintain the pH of the reaction. The reaction is completed in about 6 to 18 hours.

In preparing those compounds of formula I wherein Y is —NH—, the above-described reaction of a compound of formula II with a compound of formula III is preferably carried out in water at a pH of about 8.5 to 9 and the temperature of the reaction is maintained at about 45°–55° C. Preferably, only about two equivalents of a compound of formula III are initially used in the reaction; an additional equivalent of the compound of formula III is added in portions starting about 2 to 3 hours after the reaction begins. Total reaction time will preferably be about 8 to 24 hours. The desired trisubstitued product can be separated from the reaction mixture, which includes the mono-, di-, tri- and tetra-substituted derivatives, by art-recognized techniques including selective precipitation, chromatography and crystallization.

A preferred preparation of the compounds of formula I wherein Y is NH and $R_2$ is hydrogen is to react 1,4,7,10-tetraazacyclododecane, known in the art, with dimethylformamidedimethylacetal in the presence of benzene to yield 1,4,7,10-tetraazatricyclo [5.5.1.0]tridecane. This "tricyclic" compound is reacted with an ethanol/water mixture to yield 1-formyl-1,4,7,10-tetraazacyclododecane. This formyl compound is then reacted with t-butyl bromoacetate to yield 1-formyl, 4,7, 10-triscarboxy-methyl-1,4,7,10-tetraazacyclododecane, tris-t-butylester. Finally, the ester groups are removed in the presence of strong acid, such as sulfuric acid, to yield a compound of formula I wherein Y is NH and $R_2$ is hydrogen.

Additional synthetic approaches for preparing the compounds of this invention will be apparent to those of ordinary skill in the art. For example, those compounds of formula I wherein Y is

and $R_1$ is alkyl, arylalkyl, hydroxyakyl, aryl can be prepared by alkylation of the corresponding compound of formula I wherein Y is —NH—. Those compounds of formula I wherein Y is —NH— can be prepared by debenzylation of the corresponding compound of formula I wherein Y is

and $R_1$ is benzyl. The debenzylation reaction can be accomplished using catalytic hydrogenolysis.

Those starting compounds of formula II wherein Y is oxygen or —NH— are known. The compounds of formula II wherein Y is

and $R_1$ is alkyl, arylalkyl, hydroxyalkyl or aryl (this subgenus is referred to hereinafter as $R'_1$) are novel, and as such constitute an integral part of this invention. They can be prepared from the compound of formula II wherein Y is —NH— using conventional alkylation techniques.

Alternatively, the starting compounds of formula II wherein Y is

can be prepared by first reacting the 1,4,7-tritosylate of diethanol-amine with the 1,7-ditosylate of a 4-substituted 1,4,5-triazaheptane to yield

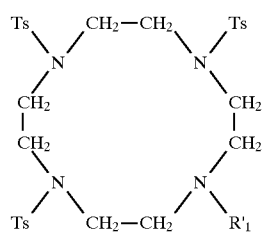

wherein the symbol "Ts" represents the tosyl (p-toluenesulfonyl) group. This general approach to polyazamacrocycles is described in *Org. Synth.*, 58:86 (1978). The 4-substituted 1,4,7-triazaheptanes can be prepared using the methodology described in U.S. Pat. No. 3,201,472.

Removal of the tosyl groups from a compound of formula IV yields the desired compounds of formula II wherein Y is

It can be accomplished by acid hydrolysis using, for example, concentrated sulfuric acid or hydrobromic acid with acetic acid and phenol or by reductive cleavage using, for example, lithium aluminum hydride or sodium in liquid ammonia.

Alternatively, the starting compounds of formula II wherein Y is

can be prepared by reducing the corresponding compound having the formula

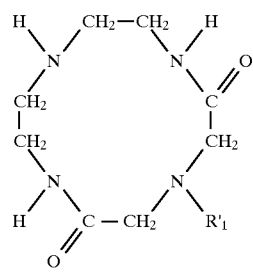

using phosphorous oxychloride or phosphorous pentachloride and zinc or sodium borohydride, lithium aluminum hydride, or borane. Compounds of formula V can be prepared by cyclocondensation of diethylenetriamine with diesters of substituted imino diacetic acids, i.e., compounds of the formula

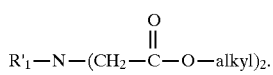

The compounds of formula I wherein Y is

$R_2$=hydrogen and $R_1$ is other than hydrogen are prepared from the compound of formula I wherein Y is

and $R_2$ is hydrogen namely, 1,4,7-triscarboxymethyl-1,4,7, 10-tetraazacyclododecane (DO3A). These type of reactions are known in the art and are described below:

For convenience "DO3A" will be represented pictorially by

in order to illustrate the reactive secondary amine nitrogen.

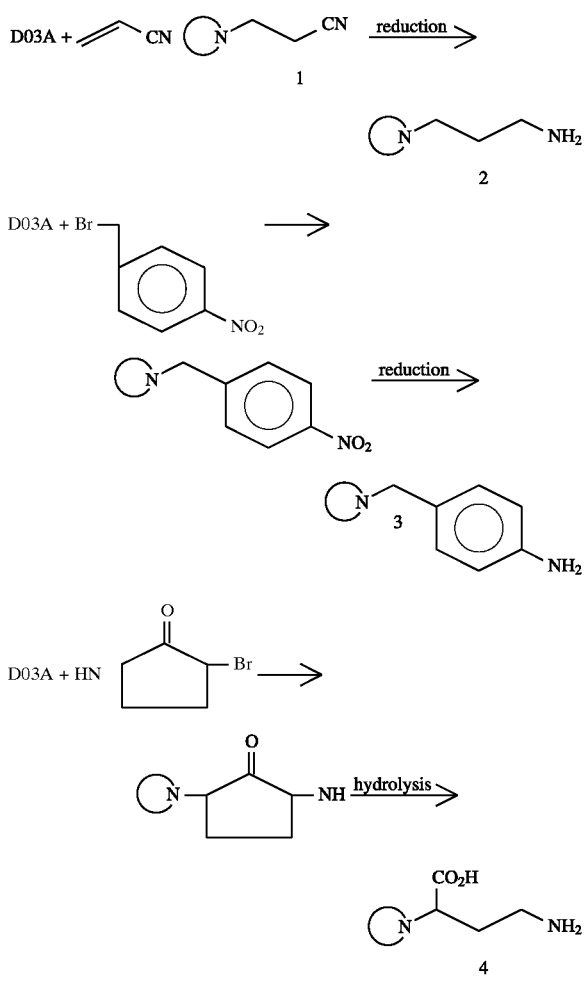

-continued

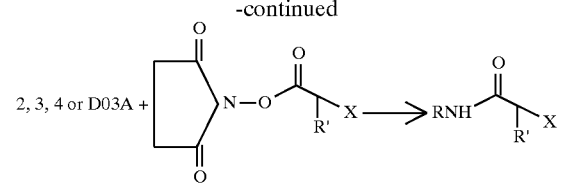

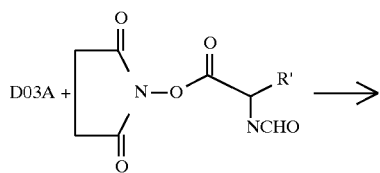

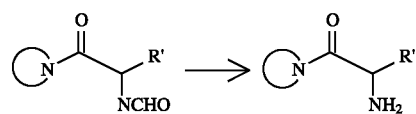

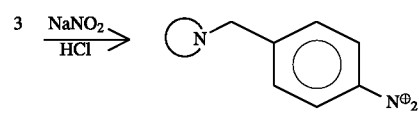

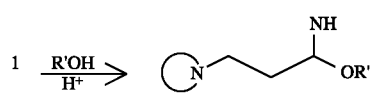

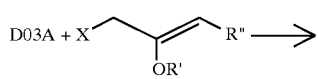

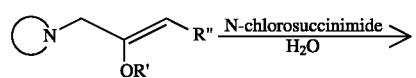

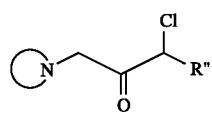

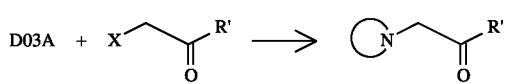

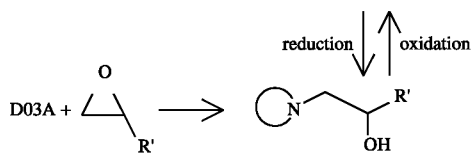

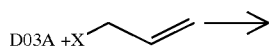

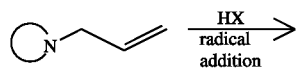

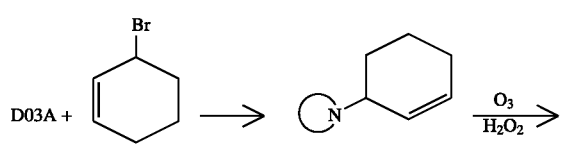

-continued

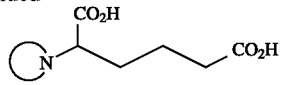

where

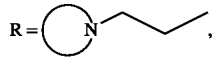

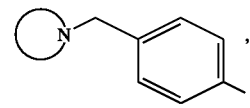

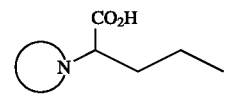

and R' and R" can be the same or different and are alkyl.

The following examples are specific embodiments of this invention.

EXAMPLE 1

4,7,10-Triscarboxymethyl-1-oxa-4,7,10-triazacyclododecane

To a solution of 8.00 g (24.8 mmol) of 1-oxa-4,7,10-triazacyclododecane sulfuric acid salt in 20 ml of water was added 6M potassium hydroxide to give a pH of 9.1. Chloroacetic acid (11.66 g, 124 mmol) was added, the pH adjusted to 9.5, and the solution warmed to 45° C. The reaction was continued for 15 hours with base added as necessary to maintain the pH between 9.5–10. The solution was cooled to 21° C., the pH brought to 2.0 with concentrated hydrochloric acid, and the solution evaporated to dryness. The residue was extracted with 400 ml of ethanol, filtered, and the solvent evaporated. The solid was dissolved in water and passed onto a cation exchange column (Dowex 50X2, hydrogen form). The column was washed with water and the ligand eluted with 0.5M ammonium hydroxide. The solvent was evaporated, the solid redissolved in water and passed onto an anion exchange column (AG1-X8, formate form). The column was washed well with water, and the ligand eluted with 0.5M formic acid. The solvent was evaporated under reduced pressure, the solid redissolved in water and reevaporated. The crude solid was dissolved in methanol and slowly precipitated by the addition of acetone and cooling to about 5° C. The yield was 2.66 g of an extremely hygroscopic and deliquescent solid. $^{13}C$ NMR ($D_2O$, ppm vs TMS): 175.4, 170.7, 65.3, 58.4, 56.0, 54.0, 53.7, 49.9. Mass spectrum (FAB): m/e 348 (M+H) and 346 (M−H).

EXAMPLE 2

1,4,7-Triscarboxymethyl-1,4,7,10-tetraazacyclododecane

Method I

A solution of 36.8 g (0.100 mol) 1,4,7,10-tetraazacyclododecane bissulfuric acid salt in 166 ml deionized water was brought to pH 8.5 using 6M potassium hydroxide. To this solution was added 18.9 g (0.200 mol) of solid chloroacetic acid, and the pH was readjusted to 8.5. The temperature was increased to 50° C. and the pH maintained between 8.5–9.0 by the addition of 6M potassium hydroxide as necessary. After 3 hours, an additional 4.73 g (0.050 mol) of chloroacetic acid was added, and the pH readjusted. After 5 hours, an additional 3.78 g (0.040 mol) of chloroacetic acid was added and the pH was readjusted. The reaction was continued at 50° C. and pH 8.5–9.0 for 16 hours after the second addition. The reaction mixture was cooled, the pH brought to 2 with concentrated hydrochloric acid, and the mixture diluted with methanol. The mixture was filtered and the filtrate evaporated. The solid was dissolved in water and passed onto a cation exchange column (Dowex 50X2-400, hydrogen form). The column was washed well with water then the ligand brought off by eluting with 0.5M ammonium hydroxide. Evaporation gave the solid ammonium salt. This salt was dissolved in water and passed onto a column of anion exchange resin (Dowex AG1-X8). The column was washed well with water and the ligand eluted with 0.5M aqueous formic acid. The solid obtained after evaporation of the solvent was crystallized from methanol to give 8.2 g of the ligand as a colorless solid. $^{13}$C NMR (D$_2$O, ppm vs TMS): 176.9, 171.0, 57.0, 55.7, 52.7, 50.3, 49.3, 43.6. Mass spectrum (FAB): m/e 345 (M–H) and 347 (M+H).

Method II

A mixture of 100 mg of 10% palladium on charcoal and 250 mg of 1-benzyl-4,7, 10-triscarboxymethyl-1,4,7,10-tetraazacyclododecane in 40 ml of 5% acetic acid in water was shaken under 35.8 p.s.i. of hydrogen for 16 hours. Filtration and evaporation gave the crude ligand which was crystallized from methanol/acetone yielding 130 mg of the desired product.

EXAMPLE 3

1-Methyl-4,7,10-triscarboxymethyl-1,4,7,10-tetraazacyclododecane

To a solution of 250 mg (0.723 mmol) of 1,4,7-triscarboxymethyl-1,4,7,10-tetraazacyclododecane in 2.9 ml of methanol was added 220 mg (1.59 mmol) of potassium carbonate. To the resulting mixture was added 308 mg (2.17 mmol, 3 equiv) of methyl iodide. Within a short time, most of the solids dissolved. After 15 hours at 21° C., a mass of crystals had separated. Additional methanol was added (2 ml) to dissolve the solid. After 23 hours, an additional 102 mg (0.72 mmol) of methyl iodide was added. After an additional 16 hours, the solution was acidified with concentrated hydrochloric acid and the volatiles were removed on the rotary evaporator. The residue was extracted with methanol, filtered, and the methanol evaporated. The residue was crystallized twice from methanol/acetone yielding 56 mg (0.16 mmol) of a colorless solid, melting point 215°–240° (dec.). $^{13}$C NMR (D$_2$O, ppm vs TMS): 177.2, 171.1, 57.2, 56.5, 54.1, 52.6, 50.1, 49.9, 43.7. Mass spectrum (FAB): m/e 359 (M–H) and 361 (M+H).

EXAMPLE 4

1-Benzyl-4,7,10-triscarboxymethyl-1,4,7,10-tetraazacyclododecane

A) 5-Benzyl-2,8-dioxo-1,5,9-triazanonane

To a solution of 6.80 g (95.7 mmol) acrylamide (95.7 mmol) in 10 ml water at ca. 5° C. was added dropwise 4.4 ml (4.32 g, 40.3 mmol) of benzyl amine. After the addition was complete, the temperature was raised to 87° C. for 6 hours. The water was evaporated to give a thick oil. The oil was dissolved in about 25 ml acetone and about 15 ml of ether was added to precipitate an oil. This mixture was allowed to stand for 16 hours, during which time the oil solidified. The solid was broken up and collected by filtration and dried under vacuum at 50° C. for 6 hours. The crude product weighed 9.75 g (39.1 mmol), melted at 103°–106° C., and was suitable for use in the next reaction without further purification.

B) 4-Benzyl-1,4,7-triazaheptane

To a solution of 38.7 g (0.586 mol) potassium hydroxide in 150 ml water at 5° C. was added 30.0 g (0.120 ml) of 5-benzyl-2,8-dioxo-1,5,9-triazanonane. To the resulting mixture was added dropwise 345 ml of 0.80M potassium hypochlorite over 0.5 hours. The solution was allowed to warm to 21° C. then heated to 85° C. for 4 hours. The solvent was then evaporated under reduced pressure and the residue was extracted with dichloromethane, filtered, dried with magnesium sulfate, filtered, and evaporated to give 14.7 g of the crude product. Vacuum distillation gave 10.1 g of the desired triamine as a colorless liquid, boiling point 110°–115° C. at 0.35 mm. of Hg. $^{13}$C NMR (CDCl$_3$, ppm vs TMS): 139.1, 128.7, 128.1, 126.9, 59.0, 56.3, 39.3. Mass spectrum (CI): m/e 194 (M+H) and 192 (M–H).

C) 4-Benzyl-1,7-bis(p-toluenesulfonyl)-1,4,7-triazaheptane

To a solution of 141.2 g (0.741 mol) of p-toluenesulfonyl chloride in 250 ml of dichloromethane with 110 ml (0.8 mol) of triethylamine was added dropwise 68.0 g (0.352 mol) of 4-benzyl-1,4,7-triazaheptane in 75 ml of dichloromethane. After 2 hours, the solution was washed three times with water at pH 9, and the organic phase was dried with sodium sulfate and filtered. Evaporation gave an oil which was dissolved in about 450 ml of ethyl acetate. The solution was diluted with 200 ml of ether and left to stand at room temperature for 24 hours. The mixture was further diluted with about 50 ml of ether and refrigerated for another day. The product crystallized in massive prisms which were collected by filtration and dried under vacuum at 40° C. for 6 hours, yielding in the first crop 140 g (0.279 mol) of a colorless solid; melting point 87°–91° C. Mass spectrum (CI): m/e 502 (M+H) and 500 (M–H).

D) 1-Benzyl-4,7,10-tris(p-toluenesulfonyl)-1,4,7,10-tetraazacyclododecane

Into a dry flask under nitrogen was placed about 3.9 g of a 60% sodium hydride dispersion. It was washed twice with hexanes then suspended in 200 ml of dry dimethylformamide. To the mixture was added 20 g (40 mmol) of 4-benzyl-1, 7-bis-(p-toluenesulfonyl)-1,4,7-triazaheptane over 5 minutes. After the initial reaction had subsided, the mixture was heated to 110° C. for 1 hour. To the resulting hot solution was added dropwise 22.6 g (40 mmol) of diethanolamine tritosylate in 100 ml of dry dimethylformamide over 3.5 hours. After an additional 0.5 hours, the solution was allowed to cool and 20 ml of methanol was added. The volatiles were then removed on the rotary evaporator. The residue was dissolved in a mixture of 400 ml of water and 200 ml of dichloromethane. The phases were separated and the aqueous phase washed twice more with dichloromethane. The combined organic fractions were dried (magnesium sulfate), filtered, and evaporated to give a yellow oil. Crystallization was induced by the addition of about 100 ml of methanol. The mixture was kept at –5° C. overnight and the product collected by filtration. After drying, 20.4 g of a colorless solid was obtained; melting point 208°–210° C.

E) 1-Benzyl-1,4,7,10-tetraazacyclododecane tetrahydrochloride

Method I

To a slurry of 2.0 g (2.8 mmol) 1-benzyl-4,7,10-tris(p-toluenesulfonyl)-1,4,7,10-tetraazacyclododecane in about 25 ml of ammonia at −77° C. under nitrogen was added 0.50 g (22 mmol, 8 equiv) of sodium metal in portions over about 5 minutes. The blue mixture was stirred an additional 45 minutes and the reaction was quenched with 1.16 g (22 mmol) of solid ammonium chloride. The ammonia was allowed to evaporate. Water (50 ml) was added to the residue and the pH adjusted to about 12 using 6M potassium hydroxide. The mixture was extracted three times with 30 ml portions of dichloromethane. The combined organic fractions were then extracted with three 30 ml portions of 2M hydrochloric acid. Evaporation of the water under reduced pressure gave a solid residue. The residue was washed with methanol and dried under vacuum at 50° C. to give 600 mg (1.47 mmol) of a colorless solid, which was used directly in the final step.

Method II 1. 1-Benzyl-3,11-dioxo-1,4,7,10-tetraazacyclododecane

To a solution of 31.2 g dimethyl-N-benzyliminodiacetate in 2.5 l of dry ethanol at reflux under nitrogen was added dropwise 12.8 g of diethylenetriamine in 160 ml of dry ethanol. Reflux was carried out for a total of 137 hours. The solution was evaporated under reduced pressure leaving a yellow paste. Trituration with acetone left 5.2 g of the desired product as a colorless solid. $^{13}$C NMR (methanol, ppm vs TMS): 173.130.5, 129.130.5, 129.6, 128.8, 64.0, 46.3, 38.7. Mass spectrum (CI): m/e 291 (M+H) and 289 (M−H).

2. 1-Benzyl-1,4,7,10-tetraazacyclododecane

To a suspension of 890 mg (3.07 mmol) of 1-benzyl-3,11-dioxo-1,4,7,10-tetraazacyclododecane in tetrahydrofuran under nitrogen was added 2.64 ml of 8M borane-methyl sulfide complex (21.1 mol, 7 equivalents). The mixture was heated to reflux allowing the methyl sulfide to distill out of the reaction flask. After 2 hours, the reaction was quenched by the addition of 12 ml 1.8M hydrochloric acid in methanol and refluxed for an additional 3 hours. Volatiles were removed by evaporation, and the solid resuspended in methanol and reevaporated. The product was crystallized from methanol/ethyl acetate; yield 455 mg, 37%. Mass spectrum (CI): m/e 263 (M+H).

F) 1-Benzyl-4,7,10-triscarboxymethyl-1,4,7,10-tetraazacyclododecane

The pH of a solution of 3.5 g of 1-benzyl-1,4,7,10-tetraazacyclododecane tetrahydrochloride in 17 ml of water was adjusted to 7 using 6.0M potassium hydroxide. To this solution was added 3.64 g of chloroacetic acid, and the pH was readjusted to 9.5. The solution was warmed to 45° C. and the pH adjusted as necessary to maintain the pH at 9.5–10. After 6 hours, the heat source was removed and the solution left to stand for 1 day. The solution was acidified to pH 3 with concentrated hydrochloric acid, diluted with 500 ml of water, and applied to a Dowex 50X-2 cation exchange resin (H$^+$ form). After washing with water, the ligand was eluted with 0.5M aqueous ammonia. After evaporation of the solvents, the crude ammonium salt was redissolved in water and applied to an anion exchange column. After washing with water, the ligand was eluted with 0.2M aqueous formic acid. After evaporation of the solvents, the crude product was crystallized from methanol/acetone to give 2.0 g of the ligand as a colorless solid. Mass spectrum (FAB): m/e 437 (M+H) and 435 (M−H).

EXAMPLE 5

Gadolinium(III)(1,4,7-triscarboxymethyl-1,4,7,10-tetraazacyclododecane)

Method I

To a solution of 9.05 g (26.1 mmol) of 1,4,7-triscarboxymethyl-1,4,7,10-tetraazacyclododecane (see Example 3) in 50 ml of water was added 4.74 g (13.1 mmol) of solid gadolinium oxide. The mixture was heated to 90° C. for 4 hours, during which time most of the solid dissolved. The mixture was filtered and the filtrate evaporated to dryness under reduced pressure. The gummy residue was twice dissolved in ethanol and evaporated to dryness. The colorless solid residue was dissolved in nitromethane, filtered through a fine porosity sintered glass funnel, and the filtrate placed in a flask in a closed container also holding about 1 liter of water. Diffusion of water into the organic solution over several days gave a colorless solid precipitate. The precipitate was collected by filtration, washed with nitromethane, resuspended in acetone and washed well with that solvent, then dried under vacuum at 60° C. for 2 days yielding 10.7 g of a colorless solid. Anal. Calcd. for 90.06% ligand, 9.94% water; C, 30.25; H, 5.28; N, 10.08. Found: C, 30.25; H, 5.48; N, 9.97; C/N=14.4

Method II

Gadolinium acetate tetrahydrate (145.5 mg) was dissolved in 3 ml of deionized water. Aqueous 1M 1,4,7-triscarboxymethyl-1,4,7,10-tetraazacyclododecane was added to the gadolinium acetate solution, mixed and adjusted to pH 3. The mixture was heated for 20 minutes at 88° C. and adjusted to pH 7.3 with 1N sodium hydroxide. The free gadolinium content was measured by paper thin layer chromatograhy. Twice the quantity of 1,4,7-triscarboxymethyl-1,4,7,10-tetraazacyclododecane required to chelate any free gadolinium was added. The solution was adjusted to pH 3, heated at 88° C. for 20 minutes and then adjusted to pH 7.3. Free gadolinium content was determined and 1,4, 7-triscarboxymethyl-1,4,7,10-tetraazacyclododecane was added as required. The sample was adjusted to 7 ml with deionized water, passed through a 0.22 μ filter (Millipore) into a vial, stoppered and sealed.

EXAMPLE 6

Gadolinium(III)(4,7,10-triscarboxymethyl-1-oxa-4,7,10-triazacyclododecane)

Thirty mg of 4,7,10-triscarboxymethyl-1-oxa-4, 7,10-triazacyclododecane (see Example 1) was added to 0.7 ml of 100 mM gadolinium acetate. The solution was adjusted to pH 3 and heated at 88° C. for 20 minutes. A precipitate was visible when the solution was adjusted to pH 7.3. 4,7,10-Triscarboxymethyl-1-oxa-4,7,10-triazacyclododecane (16 mg) was added, the solution adjusted to pH 3 and heated at 88° C. for 20 minutes. On adjustment to pH 7.3, a slight precipitate was observed. Twenty mg of 4,7,10-triscarboxymethyl-1-oxa-4,7,10-triazacyclododecane was added and the solution was adjusted to pH 3.0. Reheating under the same conditions resulted in reducing the free gadolinium to 0.22±0.18% as measured by paper thin layer chromatography of a radiolabeled chelate solution. The final chelate solution was clear at pH 7.3. It was passed through a 0.22 μ filter (Millipore) into a vial and sealed.

EXAMPLE 7

$^{99M}$Technetium(1,4,7-triscarboxymethyl-1,4,7,10-tetraazacyclododecane)

100 mM of calcium (II) (1,4,7-triscrboxymethyl-1,4,7,10-tetraazacyclododecane) was prepared by mixing equal volumes of 200 mM of calcium chloride and 200 mM of 1,4,7-triscarboxymethyl-1,4,7,10-tetraazacyclododecane.

One and one-half ml of the solution was adjusted to pH 8.8 with dilute sodium hydroxide and 150 μl of 0.88% stannous chloride was added and mixed. Technetium-99 m was added to obtain a final concentration of 20 μCi/ml and the solution was adjusted to pH 3. The solution was heated at 88° C. for 20 minutes, cooled, and adjusted to pH 7. After adjusting to a volumne of 3 ml, it was passed through a 0.22μ filter.

EXAMPLE 8

Gallium(III)(1,4,7-triscarboxymethyl-1,4,7,10-tetraazacyclododecane)

(1,4,7-Triscarboxymethyl-1,4,7,10-tetraazacyclododecane (69.3 mg) and 58.8 mg of dihydrated calcium chloride were mixed in water to yield calcium (II) (1,4,7-triscarboxymethyl-1,4,7,10-tetraazacyclododecane). 90 μCi of $^{67}$-gallium was added. The solution was adjusted to pH 3, heated at 88° C. for 20 minutes and adjusted to pH 7.3.

EXAMPLE 9

Bismuth(III)(1,4,7-triscarboxymethyl-1,4,7,10-tetraazacyclododecane)

50 mM Bismuth(III) (1,4,7-triscarboxymethyl-1,4,7,10-tetraazacyclododecane) was prepared by combining 24.2 mg of bismuth nitrate with 100 μl of 1M 1,4,7-triscarboxymethyl-1,4,7,10-tetraazacyclododecane and 140 μl of acid. The solution was adjusted to pH 3 with dilute sodium hydroxide. The mixture was heated at 88° C. until the bismuth nitrate dissolved (ca. 30 minutes). The solution was adjusted to pH 7.3 with dilute sodium hydroxide and reheated briefly at 88° C. until a small quantity of precipitate was dissolved. On cooling, the solution remained clear.

Determination of free bismuth by precipitation and x-ray fluorescence spectroscopy showed that >99% of the bismuth had been chelated.

EXAMPLE 10

Chromium, Iron, Manganese and Dysprosium Chelates of (1,4,7-triscarboxymethyl-1,4,7,10-tetraazacyclododecane)

Four hundred fifty μl of 100 mM solutions of each of chromic chloride, ferric chloride, manganese chloride and dysprosium chloride were mixed with 50 μl of 1M 1,4,7-triscarboxymethyl-1,4,7,10-tetraazacyclododecane and adjusted to pH 4.5. The solutions were heated at 88° C. for 20 minutes to enhance the rate of chelation, cooled and then adjusted to pH 7.

To determine if chelation had occurred, the solutions were diluted to a concentration of 1 mM metal chelate. An aliquot was tested by measuring its relaxivity and comparing it with the relaxivity of the metal ion alone. The data demonstrated clearly that the metal ions had been chelated. The relaxivity is proportional to the number of water molecules bound to the metal. The chelator displaces coordinated water molecules and thus lowers the relaxivity. Relaxitives of metal chelates are shown in the following table.

| Relaxivities of Metal Chelates at 20 MHz | |
|---|---|
| Chelate Metal | $K_1$ (Mole$^{-1}$ Sec.$^{-1}$) |
| Dysprosium(III)(1,4,7-triscarboxymethyl-1,4,7,10-tetraazacyclododecane) | 177 |
| Dysprosium chloride | 525 |
| Iron(III)(1,4,7-triscarboxymethyl-1,4,7,10-tetraazacyclododecane) | 530 |
| Ferric chloride | 3374 |
| Chromium(III)(1,4,7-triscarboxymethyl-1,4,7,10-tetraazacyclododecane) | 422 |
| Chromic chloride | 3270 |
| Manganese(III)(1,4,7-triscarboxymethyl-1,4,7,10-tetraazacyclododecane)(sodium salt) | 1151 |
| Manganese chloride | 6250 |

EXAMPLE 11

Gadolinium(III)(4,7,10-triscarboxymethyl-1-methyl-1,4,7,10-tetraazacyclododecane)

Gadolinium acetate tetrahydrate (102 mg) was mixed with 133 mg of 4,7,10-triscarboxymethyl-1-methyl-1,4,7,10-tetraazacyclododecane. To the mixture was added 250 μCi of $^{153}$gadolinium nitrate. The solution was adjusted to pH 3 with 1N hydrochloric acid and heated for 20 minutes at 88° C. The solution was adjusted to pH 7. Free gadolinium content was 5.07%. Additional ligand, 36 mg, was added, the solution was adjusted to pH 3 and heated as before. The solution was adjusted to pH 7.3 and tested by the thin layer chromatography procedure. Free gadolinium content was 0.14%.

EXAMPLE 12

50 mM Yttrium(III)(1,4,7-triscarboxymethyl-1,4,7,10-tetraazacyclododecane).

145.4 mg of Yttrium acetate tetrahydrate Y(OAc)$_3$(H$_2$O)$_4$ is dissolved in 3 ml of deionized water. 0.1 mCi of a radioactive tracer, $^{90}$Y in hydrochloric acid, is added. 385 μl of aqueous 1M 1,4,7-triscarboxymethyl-1,4,7,10-tetraazacyclododecane is added to the yttrium acetate solution, mixed and adjusted to pH 3 to 4 with 1N hydrochloric acid or 1N sodium hydroxide. The mixture is heated for 20 minutes at 88° C. and adjusted to pH 7.3 with 1N sodium hydroxide. The unreacted yttrium is measured by paper thin-layer chromatography. The quantity of 1,4,7-triscarboxymethyl-1,4,7,10-tetraazacyclododecane required to react with any unreacted yttrium is added by weighing the proper amount of solid 1,4,7-triscarboxymethyl-1,4,7,10-tetraazacyclododecane or by adding an additional volume of the 1M 1,4,7-triscarboxymethyl-1,4,7,10-tetraazacyclododecane solution. The solution is adjusted to pH 3 to 4, heated at 88° C. for 20 minutes and then adjusted to pH 7.3. The process of detecting unreacted yttrium and adding further aliquots of 1,4,7-triscarboxymethyl-1,4,7,10-tetraazacyclododecane is repeated until the unreacted yttrium level is less than 0.05 mM as determined by the TLC method. The sample is adjusted to 7 ml with deionized water, passed through a 0.22μ filter (Millipore) into a vial, stoppered and sealed.

EXAMPLE 13

[$^{90}$Yttrium](III)1,4,7-(triscarboxymethyl-1,4,7,10-tetraazacyclododecane)

10 mCi of $^{90}$Y in a minimum volume of [0.1M] hydrochloric acid is treated with sodium hydroxide using a micropipet until the pH is 3 to 4. µl aliquots of 1M 1,4,7-triscarboxymethyl-1,4,7, 10-tetraazacyclododecane at pH 3.5 are added to make the mixture $10^{5-}$M in 1,4,7-triscarboxymethyl-1,4,7,10-tetraazacyclododecane and then the mixture is heated for 20 minutes at 88° C. and adjusted to pH 7.3 with concentrated sodium hydroxide. The percentage of $^{90}$yttrium is determined by thin layer chromatography. If more than 0.1% of the yttrium is unreacted, the pH is lowered to 3 to 4 and the mixture again heated at 88° C. for 20 minutes. This procedure is repeated until either the level of unreacted $^{90}$Y is less than 0.1% of the total, or the level is the same after two consecutive heating cycles. If the level of unreacted $^{90}$Y is greater than 0.1% and not decreasing after two heating cycles, and additional aliquot of 1,4,7-triscarboxymethyl-1,4,7,10-tetraazacyclododecane is added to make the concentration $2\times10^{-5}$M in 1,4,7-triscarboxymethyl-1,4,7,10-tetraazacyclododecane. The heating procedure is then repeated until the level of unreacted $^{90}$Y is less than 0.1%.

The sample is adjusted with deionized water to the desired activity level, and passed through a 0.22µ filter (Millipore) into a vial and sealed.

EXAMPLE 14

Yttrium(III)1,4,7-(triscarboxymethyl-1,4,7,10-tetraazacyclododecane from $Y_2O_3$ 9 grams (26 mmol) of 1,4,7-triscarboxymethyl-1,4,7,10-tetraazacyclododecane in 50 ml of distilled water is treated with 2.95 grams of (13 mmol) $Y_2O_3$. The mixture is heated at 88° C. for 4 hours, while the solid dissolves. The solution is filtered to remove any undissolved solid and the solvent is removed by evaporation. Vacuum drying is used to obtain a dry solid. Alternatively, the filtered reaction solution may be spray dried.

EXAMPLE 15

1,4,7-Triscarboxymethyl-10-(2'-cyanoethyl)-1,4,7,-10-tetraazacyclododecane

Into a 50 ml round bottom flask was placed 5.22 g (0.0151 mol) of 1,4,7-triscarboxymethyl-1,4,7,10-tetraazacyclododecane (DO3A) and dissolved in 21 ml of water. The pH of the solution was raised to 8.28 with 6N NaOH. Then 1.35 ml (1.09 is g, 0.0205 mol) of acrylonitrile was added and the reaction allowed to stir overnight at room temperature. The reaction is then concentrate in vacuo, and then re-dissolved in methanol and concentrated in vacuo.

EXAMPLE 16

1,4,7-Triscarboxymethyl-10-(2'-carboxyethyl)-1,4,7,10-tetraazacyclododecane

The crude product of a 0.015 mol preparation of Example 15 was added to 100 ml of 3N NaOH (large excess) and heated to 85° C. and allowed to stir under nitrogen for five hours. The inorganic salts are then removed via cation/anion exchange chromatography as described in Example 2, Method I.

EXAMPLE 17

1,4,7-Triscarboxymethyl)-10-(3'-aminopropyl)-1,4,7,10-tetraazacyclododecane 0.5 g of the crude reaction product of Example 15 was dissolved in 25 ml of water and to this was added 1 ml of conc. HCl. This solution was then added to 0.25 g of 10% Pd/C and then hydrogenated at approximate 40 psi overnight. The cataylst was then filtered over a Celite bed and the solution concentrate in vacuo.

EXAMPLE 18

1,4,7-Triscarboxymethyl-1,4,7,10-tetraazacyclododecane (DO3A)

A) 1,4,7,10-tetraazatricyclo[5.5.1.0]tridecane

Reagents a. 1,4,7,10-tetraazacyclododecane 250 g (1.45 moles)
b. Benzene (sieve-dried) 2.5 liters
c. Dimethyl formamidedimethylacetal 173 g (1.45 moles)

The above were combined and heated in an oil bath at 80° C. under nitrogen while the benzene-methanol azeotrope (64° C.) distilled off. After ninety minutes, the temperature of the distillate rose to 80° C. indicating complete reaction. Distillation of benzene was continued for an additional thirty minutes to ensure complete reaction. The reaction mixture was concentrated in vacuo (50° C.) then the residue distilled (bath temperature 160° C.) to yield 253 g (96%) of desired product. b.p. 128°–130° C./0.5 mm.

B) 1-formyl-1,4,7,10-tetraazacyclododecane

Reagents

| a. 1,4,7,10-tetraazatricyclo[5.5.1.0]tri-decane | 246 g |
|---|---|
| b. Absolute ethanol | 500 ml |
| c. $H_2O$ | 500 ml |

The product of A was chilled in an ice bath (4° C.) then treated with ethanol-water (pre-mixed) which had been chilled to −20° C. The mixture was allowed to slowly warm to room temperature then stirred under nitrogen for twenty-four hours at ambient temperature. The reaction mixture was concentrated in vacuo. The residue was dissolved in acetonitrile (1,000 ml) then concentrated in vacuo. This operation was repeated three times (3×1,000 ml) to remove all traces of water. The residue was dried in vacuo at room temperature overnight. After four hours the material crystallized with significant heat of crystallization. Yield 270 g (100%).

C) 1-formyl,-4,7,10-triscarboxymethyl,-1,4,7,10-tetraazacyclododecane,tris-t-butyl ester To the product of B, dissolved in dimethylformamide, was added 4 equivalents of t-butyl bromoacetate. An initial exotherm was controlled by ice bath cooling, and after 30 minutes solution of sodium carbonate was added. After agitating this mixture briskly for an additional 30 minutes, toluene is added and the reaction is allowed to proceed at 30° C. until complete by TLC.

After agitation is stopped, the layers are allowed to settle and the lower aqueous layer, containing mainly DMF and salts, is withdrawn. Further extraction of the toluene layer with aqueous sodium carbonate effects removal of any remaining DMF. The toluene solution is treated with 1 equivalent of dilute HCl to extract the intermediate formyl triester into water, and to separate excess t-butyl bromoacetate, which remains in the toluene layer.

Methylene chloride is added to the acidic aqueous layer, and sodium carbonate is added slowly as the mixture is rapidly agitated. Once a solution pH of 9.5 is reached, agitation is stopped and layers are allowed to form. The lower, rich methylene chloride solution is withdrawn. Additional methylene chloride is added to extract the remaining aqueous layer, and the combined organic layers are then backwashed with fresh deionized water. The methylene chloride solution containing formyl triester is concentrated.

D) 1,4,7,-Triscarboxymethyl-1,4,7,10-tetraazacyclododecane

The methylene chloride concentrate from above is added over 30–40 minutes to 2 equivalents of sulfuric acid in water, maintained at 55°–60° C. under a vigorous nitrogen sparge. Once addition is completed, the temperature and sparge are continued, with occasional replacement of water lost to evaporation, until reaction is judged to be complete by HPLC (usually 4 to 5 hours).

To remove formic acid generated during deprotection, the reaction mixture is concentrated in vacuo at no more than 40° C., until a thick viscous oil is formed. Water is added and the solution is reconcentrated to residue; this is repeated until little or no formyl proton resonance is evident by NMR (usually after 3–4 reconcentrations), and is typically accompanied by partial crystallization of DO3A as a sulfate salt.

After full dissolution in a minimum volume of water, the DO3A sulfate salt is applied to a pretreated column of poly(4-vinylpyridine). The title compound, free of sulfate, is eluted from the column with deionized water. The aqueous solution is concentrated, and optionally lyophilized to provide the product as a hygroscopic solid.

EXAMPLE 19

Gd(III) complexes of the chelating ligands of examples 15, 16 and 17 were prepared as in example 5. Purification was by standard ion exchange chromatography.

EXAMPLE 20

1,4,7-Tris(carboxymethyl)-10-(N-methylcarbamoyl-methyl)-1,4,7,10-tetraazacyclododecane A solution of 1,4,7-triscarboxymethyl-1,4,7,10-tetraazacyclododecane 7.08 g (about 19 mmol assuming 5% water content) in 68 ml $H_2O$ was adjusted to pH 8 using KOH. To it was added 4.4 g (40 mmol) $ClCH_2CONHCH_3$. The solution was warmed to 50° and the pH adjusted to 9.5 and the pH was maintained between 9–10 by the addition of KOH as required. After 23 hours the solution was cooled to room temperature, acidified to pH 3, then applied to a 500 ml bed volume of Dowex 50-X2 cation exchange resin ($H^+$ form). The column was washed with eight volumes of water then the product eluted with two volumes of 0.5$\underline{M}$ $NH_3$. Evaporation gave a yellow glassy solid. This solid was taken up in MeOH and the product precipitated with acetone. Obtained was 3.95 g of the title compound as a slightly yellow solid.

EXAMPLE 21

Gadolinium(III)(1,4,7-Tris(carboxymethyl)-10-(N-methylcarbomoylmethyl)-1,4,7,10-tetraazacyclododecane)

The pH of a mixture of 3.47 g of the crude ammonium salt from Example 20 (8.33 mmol assuming 100% of the tris $NH_3$ salt) and 1.58 g $Gd_2O_3$ (4.37 mmol) in 33 ml water was adjusted to a pH of 4 using glacial acetic acid. The mixture was heated with stirring to 100° C. for 2 hours dissolving most of the solid. The mixture was cooled and the slight amount of remaining solid removed by filtration through a 0.2 micron filter. The filtrate was passed through a 500 ml bed of Chelex 100 (ammonium form), then through a 500 ml bed column of AG1-X8 anion exchange resin (formate form). The solution was concentrated and the product further purified by preparative HPLC. Evaporation gave 3.1 g of the title compound as a colorless solid (5.2 mmol, 63% calculated for 3.5% water). The complex may be recrystallized from water.

EXAMPLE 22

1,4,7-Triscarboxymethyl-10-(2'-hydroxypropyl)-1,4,7,10-tetraazacyclododecane

To a solution of 1,4,7-triscarboxymethyl-1,4,7,10-tetraazacyclododecane 5.19 g (14.3 mmol assuming 5% water) in 30 ml water was added 2.4 g (6.0 mmol) NaOH; the pH of resulting solution was then 12.2. The solution was cooled to room temperature then 1.3 g (2.3 mmol, 1.5 equiv.) of propylene oxide was added. The stoppered flask was left to stir at room temperature for 14 hours. HPLC analysis at that point indicated a small amount of starting material so an additional 0.25 g (4.3 mmol, 0.28 equiv.) of propylene oxide was added. After 4 hours, the reaction solution was acidified to pH 2.9 with concentrated HCl, diluted to 0.5 liters with water, then applied to a 5×40 cm column of Dowex 50X-2 cation exchange resin ($H^+$ form). The column was washed with six liters of water then the product was eluted with 0.5 $\underline{M}$ $NH_3$. Obtained after rotary evaporation was 5.9 g of the title product as the ammonium salt.

EXAMPLE 23

Gadolinium(III)(1,4,7-tricarboxymethyl-10-(2'-hydroxypropyl)-1,4,7,10-tetraazacyclododecane)

To a solution of 5.6 g of the crude ammonium salt of Example 22 in 30 ml water was added 6.70 g (16.5 mmol) of $Gd(OAC)_3.4H_2O$. After 14 hours, the pH of the solution was adjusted from 4.5 to 7.0 with dilute NaOH. A solution of 1.5 g (4.0 mmol) $Na_2EDTA$ in 10 ml $H_2O$ (pH adjusted to 7.5 with dilute NaOH) was added and the resulting solution allowed to stand for 6 hours. After dilution to 0.5 liters with water the solution was applied to a 5×40 cm column of BioRad AG1-X8 anion exchange resin (formate form). After loading, the column was eluted with 1 liter of water. The total volume of eluent was collected as one fraction. Evaporation gave the title compound as a white solid. The complex was further purified by preparative HPLC. Obtained was 4.6 g of a colorless solid (12.3% water, 7.2 mmol). The complex was recrystallized from $CH_3CN$.

EXAMPLE 24

1,4,7-Tris(carboxymethyl)-10-(2'-cyanoethyl)-1,4,7,10-tetraazacyclododecanatogadolinium Into a 100 ml round bottom flask containing 40 ml of $H_2O$ was placed 4.0 g (10 mmol) of crude material from example 15 and 4.5 g (11 mmol, 1.1 eq.) of $Gd(OAc)_3.4H_2O$. The pH of the solution was 4.85. The mixture was allowed to stir at room temperature for 14 hours. The reaction solution was then analyzed via HPLC for both free ligand and for free gadolinium. The sample was found to contain a large excess (>20%) of free metal and no detectable amount of free ligand. The pH of the solution was increased to 6.95 with dilute NaOH resulting in a white suspension. The suspension was filtered through a 0.22 micron filter and the solution purified via preparative HPLC. The major peak from each injection was collected and the solution concentrated on a rotary evaporator to yield 4.2 g of the gadolinium complex as a white solid. Analysis of this material indicated that an unacceptable amount (5%) of free gadolinium was still present. The sample was dissolved in 420 ml of $H_2O$ and the pH of the solution adjusted to 7.5 with dilute NaOH. The solution was applied to a 75 ml (2.5 cm × 13 cm) column bed of Chelex-100 ($NH_4^+$ form) at a flow rate of 20 ml/min. The column was rinsed with 1 L of $H_2O$ and the effluent collected and concentrated on a rotary evaporator to yield a white solid. The solid was found to contain less than 0.1% free gadolinium. However, there was a small impurity of an unidentified gadolinium complex. The material was subsequently repurified via preparative HPLC. The desired peak was collected and concentrated on a rotary evaporator, dissolved in anhydrous methanol and then taken to dryness on a rotary evaporator and put under high vacuum for 14 hours at room temperature to yield 3.0 g (54%) of 1,4,7-tris (carboxymethyl)-10-(2'-cyanoethyl)-1,4,7,10-tetraazacyclododecanatogadolinium, as a hygroscopic white solid.

EXAMPLE 25

1,4,7-tris(carboxymethyl)-10-carbamoylmethyl 1,4,7,10-tetraazacyclododecane

The pH of a solution of 1.40 g of 1,4,7-tris (carboxymethyl)-1,4,7,10-tetraazacyclododecane in about 4 ml water was adjusted to 9.5 using 40% aqueous benzyltrimethylammonium hydroxide. To the resulting solution was added 412 mg α-chloroacetamide. The temperature was increased to 80° C. and base was added as necessary to maintain the pH at 9.5–10. After 3 hours the solution was cooled to room temperature and acidified to pH 3 with concentrated HCl. The resulting solution was evaporated under reduced pressure to a colorless sludge. The mixture was taken up in about 25 ml MeOH and re-evaporated. The thick residue was triturated with a 1:1 mixture of acetone and ethanol to provide a granular solid and colorless solution. The solid was collected by filtration, washed with acetone/ethanol followed by acetone and finally ether, then dried in a vacuum oven at 50° for 2 hours. Obtained was 1.54 g of the title compound as a colorless powder. The product was twice crystallized from ethanol/water.

Anal Calcd for $C_{16}H_{31}N_5O_7Cl_2$+1% $H_2O$: C, 39.94; H, 6.61; N, 14.55 Found: C, 39.96; H, 6.74; N, 14.33

EXAMPLE 26

1,4,7-Tris(carboxymethyl)-10-carbamoylmethyl-1,4,7,10-tetraazacyclododecanatogadolinium A mixture of 87 mg of 1,4,7-tris(carboxymethyl)-10-carbamoylmethyl-1,4,7,10-tetraazacyclododecane and 40 mg of $Gd_2O_3$ in 0.8 ml water was heated to 80° C. for 3 hours. After cooling to room temperature, the slightly cloudy solution was clarified by filtration through a 0.22 micron filter. The water was removed under reduced pressure. The residue containing the title compound was crystallized from a mixture of $H_2O$/EtOH/$CH_3CN$ (1:2:4).

Anal Calcd for $C_{16}H_{26}N_5O_7Gd$+6.18% $H_2O$: C, 32.33; H, 5.10; N, 11.78 Found: C, 32.59; H, 5.10; N, 11.62; $H_2O$ 6.18

EXAMPLE 27

1,4,7-tris(carboxymethyl)-10-(4-nitro)benzyl-1,4,7,10-tetraazacyclodedecane

To a suspension of DO3A (1.02 g, 2.93 mmol) and $K_2CO_3$ (1.22 g, 8.81 mmol) in 10 ml DMF/$H_2O$ (5:3) was added a solution of 4-nitrobenzylbromide (866 mg, 4.01 mmol) in 3 ml of DMF. The suspension was stirred at 60° C. for 24 hours which yielded a solution containing a small amount of insoluble material. The solution was evaporated under vacuum and resuspended in 20 ml $H_2O$. The suspension was acidified to pH 3 with 2M HCl and extracted with 2×10 ml ethyl acetate. The aqueous layer was evaporated under vacuum to a solid and redissolved in 50 ml $H_2O$. This solution was loaded onto a column (2.5×13 cm) of Dowex 50WX8 cation exchange resin prepared in the acidic form. After washing the column with $H_2O$ (ca. 500 ml), the column was eluted with 0.5M $NH_4OH$ (ca. 500 ml). The effluent was collected in one fraction and evaporated under vacuum to afford 1.35 g of crude product as the ammonium salt.

The ammonium salt (508 mg, 1.02 mmol) was dissolved in 5 ml $H_2O$ and adjusted to pH 8.4 with dilute $NH_4OH$. This was placed on a column. (1.5×25 cm) of AG-1X8 anion exchange resin prepared in the formate form. The column was washed with $H_2O$, then the ligand was eluted with 250 ml of 0.5M $HCO_2H$. The effluent was collected as one fraction and evaporated under vacuum to afford a glassy solid. This solid was redissolved in 100 ml of $H_2O$, evaporated to dryness, then crystallized from 5 ml $H_2O$ to yield 214 mg (40.4% based on DO3A of the title compound as a colorless solid. The compound was pure by $^1H$ and $^{13}C$ NMR. HPLC analysis showed trace impurities (<5%).

Anal Calcd for $C_{21}H_{31}N_5O_8$.12.59%$H_2O$: C, 45.71; H, 6.22; N, 12.63. Found: C, 45.78, H, 7.08; N, 12.72

EXAMPLE 28

1,4,7-tris(carboxymethyl)-10-(4-amino)benzyl-1,4,7,10-tetraazacyclododecanatogadolinium To a solution of 1,4,7-tris(carboxymethyl)-10-(4-nitro) benzyl-1,4,7,10-tetraazacyclododecanane, (193 mg, 0.40 mmol) in 5 ml $H_2O$) was added solid $Gd(OAc)_3$.4$H_2O$ (219 mg, 0.54 mmol). The resulting solution was stirred at 60° C. for 2 hours, then adjusted to pH 7.0 with 1.0M tris base and stirred for an additional 1 hour. The reaction solution was diluted to 10 ml with $H_2O$ and placed in a Parr bottle containing 200 mg of Raney Nickel, washed to neutral pH with $H_2O$ suspended in 3 ml $H_2O$. The complex was hydrogenated under 20 p.s.i.g $H_2$ for 3 hours. The catalyst was removed by centrifugation and the supernatant (pH 6.7) was filtered through a 0.2 micron filter. This solution was evaporated under vacuum to afford 564 mg of a solid. The solid was dissolved in 2 ml of $H_2O$ and placed on a column (1.0×20 cm) of Diaion CHP20P reversed phase resin packed in $H_2O$. After eluting the column with $H_2O$ (100 ml), the solvent was changed to 50% MeOH by use of a linear gradient (100 ml). Elution of the complex was detected by UV (280 nm) and collected in one fraction. This was evaporated under vacuum to yield 176 mg (72% based on starting ligand) of the title compound.

Anal Calcd for $C_{21}H_{30}N_5O_6Gd$.13.84%$H_2O$: C, 35.87; H, 5.80; N, 9.96 Found: C, 35.56; H, 5.51; N, 10.05

EXAMPLE 29

1,4,7-tris(carboxymethyl)-10-(4-isothiocyanato)-benzyl-1,4,7,10-tetraazacyclododecane To a solution of 1,4,7-tris(carboxymethyl)-10-(4-amino) benzyl-1,4,7,10-tetraazacyclododecanatogadolinium (37.8 mg, 0.06 mmol) in 2 ml $H_2O$ was added 1.0 mL of a 104 mM (0.15 mmol) solution of thiophosgene in $CHCl_3$. The biphasic mixture was stirred at 40° C. for 5 minutes then at room temperature for 1 hour. The aqueous layer was removed and evaporated under vacuum to afford 39.1 mg (96.5%) of the title compound.

This compound may be exchange labelled with $^{90}Y$ and used directly to react with antibodies or other proteins which contain free lysine groups.

EXAMPLE 30

1,4,7-Tris(carboxymethyl)-10-(2'-carboxy)ethyl-1,4,7,10-tetraazacyclododecanatogadolinium Into a 50 ml round bottom flask containing 10 ml of $H_2O$ was dissolved 1.93 g (5.58 mmol) of DO3A. The pH of the solution was adjusted to 8.3 with dilute NaOH. Then 0.47 g (9.0 mmol, 1.6 eq.) of acrylonitrile was added and the solution allowed to stir overnight at room temperature for 16 hours. The solution was then taken to dryness on a rotary evaporator and the white solid dissolved in 20 ml of $3\underline{N}$ NaOH. The solution was allowed to stir at 85° C. for 6 hours under nitrogen. The solution was adjusted to pH 4.5 with 2 $\underline{M}$ HCl, then applied to a 2.5×20 cm column of Dowex 50X-2 ($H^+$form). The column was eluted with 0.5 L of $H_2O$ and the compound eluted off the column with 0.5 L of 0.5 $\underline{M}$ $NH_4OH$. The eluate was collected as one fraction and evaporated under vacuum to a solid. The solid was evaporated (2×) from 25 ml of $H_2O$ to yield 2.52 g of the ammonium salt of the title compound.

Into a 50 ml round bottom flask containing 1.96 g of the ammonium salt described above (4.3 mmol based on a diammonium salt) was added 10 ml of $H_2O$ and 0.94 g of $Gd_2O_3$ (2.6 mmol). The resulting suspension was stirred at 100° C. for 6 hours. The insoluble $Gd_2O_3$ was removed by centrifugation and the solution was adjusted to pH 7 with 1 $\underline{M}$ acetic acid. This solution was combined with another solution of the title compound prepared similarly and passed through a 1.0×30 cm column of Chelex-100 ($NH_4^+$form). The effluent was collected as one fraction and the solution was concentrated to 20 ml on a rotary evaporator. The solution was then purified via preparative HPLC, the major peak collected and concentrated to dryness on a rotary evaporator to yield 1.99 g of 1,4,7-tris(carboxymethyl)-10-(2'-carboxymethyl)-1,4,7,10-tetraazacyclododecanatogadolinium (68% based on ligand).

EXAMPLE 31

1,4,7-Tris(carboxymethyl)-10-(3'-aminopropyl)-1,4,7,10-tetraazacyclodedecane Into a 100 ml round bottom flask containing 5.2 g of DO3A dissolved in 22 ml of $H_2O$ (pH adjusted to 8.25 with dilute NaOH) was added 1.35 ml of acrylonitrile. The reaction was allowed to stir at room temperature for 14 hours. After 14 hours, HPLC analysis inidcated complete conversion to 1,4,7-tris(carboxymethyl)-10-(2'-cyanoethyl)-1,4,7,10-tetraazacyclododecane. The reaction mixture was taken to dryness on a rotary evaporator to yield a glassy solid. The solid was dissolved in methanol and then taken to dryness on a rotary evaporator to yield 5.9 g of crude 1,4,7-tris(carboxymethyl)-10-(2'cyanoethyl)-1,4,7,10-tetraazacyclododecane as a white solid. 3.0 g of the crude 1,4,7-tris(carboxymethyl)-10-(2'-cyanoethyl)-1,4,7,10-tetraazacyclododecane was dissolved in 150 ml of $H_2O$, and the solution acidified with 6 ml of concentrated HCl. The solution was then added to a 500 ml hydrogenation vessel containing 1.5 g of 10% Pd/C and the reaction mixture hydrogenated at 50 psi $H_2$ at room temperature for 14 hours. After 14 hours the catalyst removed over a Celite bed and the filtrate taken to dryness on a rotary evaporator. The sample was dissolved in 200 ml of $H_2O$ and applied to a 2.5×20 cm column of Dowex 50X-2 ($H^+$ form). The column was eluted with 4 $\underline{L}$ of 0.5 $H_2O$ and the material eluted off the column with 1.0 $\underline{L}$ of $0.5\underline{M}$ $NH_4OH$. The eluant was concentrated to dryness on a rotary evaporator, the residue dissolved in methanol and taken to dryness on a rotary evaporator to yield 3.8 g of the ammonium salt of 1,4,7-tris (carboxymethyl)-10-(3'-aminopropyl)-1,4,7,10-tetraazacyclododecane.

EXAMPLE 32

1,4,7-Tris(carboxymethyl)-10-(3'-aminopropyl)-1,4,7,10-tetraazacyclododecanatogadolinium Into a round bottom flask containing 1.0 g of the ammonium salt of 1,4,7-tris(carboxymethyl)-10-(3'-aminopropyl)-1,4,7,10-tetraazacyclododecane in 5 ml of $H_2O$ was added 1.1 g (0.0027 mmol) of $Gd(OAc)_3.4H_2O$ and the reaction was allowed to stir at room temperature for 14 hours. After 14 hours the pH of the solution was adjusted to 7.0 with dilute NaOH and filtered through a 0.22 micron filter. The filtrate was then purified on a C-18 reverse-phase preparative HPLC using a 98% $H_2O$ and 2% $CH_3CN$ eluent. The major peak collected and concentrated to dryness on a rotary evaporator to yield 1,4,7-tris(carobyxmethyl)-10-(3'-aminopropyl)-1,4,7,10-tetraazacyclododecanatogadolinium.

EXAMPLE 33

1,4,7-Tris(carboxymethyl)-10-[N-(2-hydroxyethyl)-carbamoylmethyl]-1,4,7,10-tetraazacyclododecane A solution of 5.0 g (13.3 mmol adjusted for 8.1% $H_2O$) of DO3A in 50 ml of $H_2O$ was adjusted to pH 8.5 using $5\underline{M}$ KOH. To this was added a solution of 3.98 g (28.9 mmol) of $\underline{N}$-(2-hydroxyethyl)-chloroacetamide in 10 ml of $H_2O$. The resulting solution was adjusted to pH 9.5 and stirred at 80° C. for 24 hours. The pH was maintained at 9.5–9.7 by occasional addition of $5\underline{M}$ KOH. The solution was then cooled to room temperature and adjusted to pH 3.5 using concentrated HCl. The acidic solution was diluted to 200 ml with $H_2O$ and applied to a 4.5×20 cm column of Dowex 50X-2 strong cation exchange resin, $H^+$ form. The column was washed with 2 $\underline{L}$ of $H_2O$ and the material eluted off the column with 800 ml of $0.5\underline{M}$ $NH_4OH$. Rotary evaporation of the $NH_4OH$ fraction gave 6.5 g of the crude ammonium salt of the title compound.

EXAMPLE 34

1,4,7-Tris(carboxymethyl)-10-[N-(2-hydroxyethyl)-carbamoylmethyl]-1,4,7,10-tetraazacyclododecanatogadolinium To a solution of 5.0 g of the crude ammonium salt of Example 33 in 60 ml of $H_2O$ was added 2.04 g of $Gd_2O_3$. The mixture was adjusted to pH 4 using glacial acetic acid and stirred at 100° C. for 5 hours. The resulting cloudy solution was cooled to room temperature and filtered through a 0.2 micron filter. The filtrate was adjusted to pH 9 with concentrated $NH_4OH$ and applied to a 2.5×25 cm column of Chelex-100, ammonium form. The column was eluted with 600 ml of $H_2O$. The eluant was collected and further diluted with an additional 200 ml of $H_2O$, adjusted to pH 9 using concentrated $NH_4OH$, and applied to a 2.5×30 cm column of AG1-X8 (strong anion exchange resin, formate form). The column was eluted with 700 ml of $H_2O$, and the eluate was concentrated to dryness on a rotary evaporator. The product was then purified via preparative HPLC. The major fraction collected and evaporated to dryness on a rotary evaporator. The residue was then dissolved in 25 ml of EtOH and treated with 0.5 g of activated carbon. The moisture filtered and concentrated to dryness on a rotary evaporator to yield 3.5 g of the title complex as an off-white glassy solid.

What we claim is:

1. A complex for imaging mammalian tissue, comprising a paramagnetic ion and a tetraazacyclo compound, the complex being charge neutral in aqueous solution.

2. The complex of claim 1, wherein the Keq ($M^{-1}$) (25° C.; aqueous solution) for the complex is over 20.

3. The complex of claim 1, wherein the Keq ($M^{-1}$) (25° C.; aqueous solution) for the complex is over 23.

4. The complex of claim 1, wherein the aqueous conductivity for the complex (mho.cm$^2$.mmol$^{-1}$, 25° C.) is less than 10.

5. The complex of claim 1, wherein the aqueous conductivity for the complex (mho.cm$^2$.mmol$^{-1}$, 25° C.) is less than 2.

6. The complex of claim 1, wherein the osmolality of the complex (Osmol/kg water, 37° C.) in a 0.5M aqueous solution is less than 1.

7. The complex of claim 1, wherein the osmolality of the complex (Osmol/kg water, 37° C.) in a 0.5M aqueous solution is less than 0.65.

8. The complex of claim 1 that is bonded to a biologically active entity.

9. The complex of claim 8 wherein the biologically active entity is selected from the group consisting of bile acids, fatty acids, lipids, sugars and other alcohols, amino acids, peptides, and monoclonal antibodies and other proteins.

10. The complex of claim 1, wherein the complex in aqueous solution is stable, dissolved and the complex remains in solution when in a concentration of over 0.5M at 20°–37° C.

11. The complex of claim 1, wherein the complex in aqueous solution is stable, dissolved and the complex remains in solution when in a concentration of over 0.75M at 20°–37° C.

12. The complex of claim 1 wherein the tetraazacyclo compound is 1-substituted-1,4,7-tricarboxymethyl-1,4,7,10-tetraazaccyclododecane.

13. The complex of claim 1 wherein the complex in aqueous solution at a concentration of 0.5M has a falling ball viscosity of less than 1.5 poise at 25° C.

14. A complex used for imaging mammalian tissue, comprising a metal ion selected from the group consisting of a stable isotope of the lanthanides, tantalum, bismuth or other element with a molecular weight higher than iodine, and a tetraazacyclo compound, the complex being charge neutral in aqueous solution.

15. The complex of claim 14, wherein the aqueous conductivity for the complex (mho.cm$^2$.mmol$^{-1}$, 25° C.) is less than 10.

16. The complex of claim 14, wherein the osmolality of the complex (Osmol/kg water, 37° C.) in a 0.5M aqueous solution is less than 1.

17. The complex of claim 14, wherein the complex in aqueous solution is stable, dissolved and the complex remains in solution when in a concentration of over 0.5M at 20°–37° C.

18. The complex of claim 14 wherein the tetraazacyclo compound is 1-substituted-1,4,7-tricarboxymethyl-1,4,7,10-tetraazacyclododecane.

19. The complex of claim 14 wherein the complex in aqueous solution at a concentration of 0.5M has a falling ball viscosity of less than 1.5 poise at 25° C.

* * * * *

UNITED STATES PATENT AND TRADEMARK OFFICE
CERTIFICATE OF CORRECTION

| | |
|---|---|
| PATENT NO. | : 5,846,519 |
| APPLICATION NO. | : 08/471591 |
| DATED | : December 8, 1998 |
| INVENTOR(S) | : Michael F. Tweedle et al. |

It is certified that error appears in the above-identified patent and that said Letters Patent is hereby corrected as shown below:

Title page,
Item [54], Title, "Method For Imaging Mammalian Tissue Using "1"-substituted-1,4,7-tricarboxymethyl-1,4,7,10-tetraazacyclododecane And Analogs" should read --Method For Imaging Mammalian Tissue Using -- 10 -- -substituted-1,4,7-tricarboxymethyl-1,4,7,10-tetraazacyclododecane And Analogs.--

Claims,
Col. 28; Claim 12, line 2, "The complex of claim 1 wherein the tetraazacyclo compound is "1"-substituted-1,4,7-tricarboxymethyl-1,4,7,10-tetraazacyclododecane", should read --The complex of claim 1 wherein the tetraazacyclo compound is -- 10 -- -substituted-1,4,7-tricarboxymethyl-1,4,7,10-tetraazacyclododecane.--

Col. 28; Claim 18, line 26, "The complex of claim 14 wherein the tetraazacyclo compound is "1"-substituted-1,4,7-tricarboxymethyl-1,4,7,10-tetraazacyclododecane", should read --The complex of claim 14 wherein the tetraazacyclo compound is -- 10 -- -substituted-1,4,7-tricarboxymethyl-1,4,7,10-tetraazacyclododecane.--

Signed and Sealed this

Eighteenth Day of September, 2007

JON W. DUDAS
*Director of the United States Patent and Trademark Office*